(12) United States Patent  (10) Patent No.: US 8,563,728 B2
Mallela et al.  (45) Date of Patent: Oct. 22, 2013

(54) PROCESS FOR THE PREPARATION OF DUTASTERIDE

(75) Inventors: Sambhu Prasad Sarma Mallela, Hyderabad (IN); Sukumar Nandi, Hyderabad (IN); Balanarasimha Reddy Gona, Hyderabad (IN); Naresh Akkina, Hyderabad (IN); Rani Ananta, Hyderabad (IN); Islam Aminul, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 13/261,135

(22) PCT Filed: Jul. 7, 2010

(86) PCT No.: PCT/IB2010/001661
§ 371 (c)(1),
(2), (4) Date: Feb. 29, 2012

(87) PCT Pub. No.: WO2011/004242
PCT Pub. Date: Jan. 13, 2011

(65) Prior Publication Data
US 2012/0157683 A1 Jun. 21, 2012

(30) Foreign Application Priority Data
Jul. 9, 2009 (IN) .......................... 1634/CHE/2009

(51) Int. Cl.
*C07D 221/18* (2006.01)
(52) U.S. Cl.
USPC .......................................... 546/77
(58) Field of Classification Search
USPC .......................................... 546/77
See application file for complete search history.

(56) References Cited

U.S. PATENT DOCUMENTS

2009/0203724 A1* 8/2009 Tombari et al. ............... 514/284

* cited by examiner

*Primary Examiner* — Charanjit Aulakh
(74) *Attorney, Agent, or Firm* — Patent Science LLC; Jay R Akhave

(57) ABSTRACT

The present invention provides an improved process for the preparation of Dutasteride (I) which comprises: (i) reacting 4-aza-5α-androst-1-en-3-one-17β-carboxylic acid (VII), Formula VII with sulfonic acid anhydride $(RSO_2)_2O$ in presence of base to produce an intermediate compound of Formula (XIII), wherein R represents $C_{1-6}$ alkyl, $C_{1-6}$ halo alkyl, $C_{6-10}$ aryl, halo aryl; (ii) condensing compound of Formula (XIII) with 2,5-bis(trifluoromethyl)aniline (III), Formula (III) in the presence or absence of a base to produce Dutasteride (I).

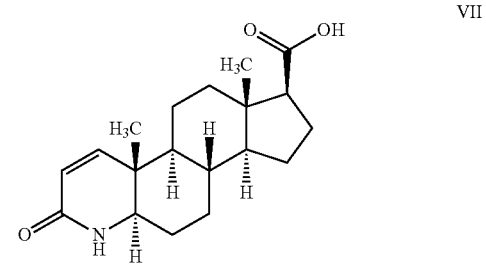

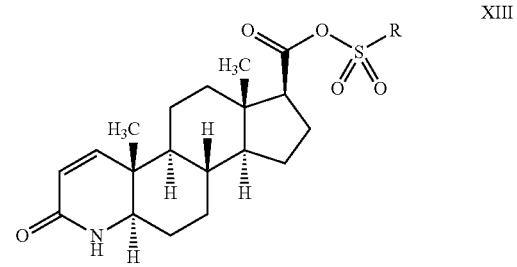

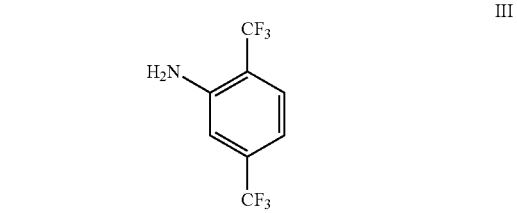

19 Claims, No Drawings

PROCESS FOR THE PREPARATION OF DUTASTERIDE

FIELD OF THE INVENTION

The present invention relates to an improved process for the preparation of (5α,17β)-N-[2,5-bis(trifluoromethyl)phenyl]-3-oxo-4-azaandrost-1-ene-17-carboxamide of Formula (I).

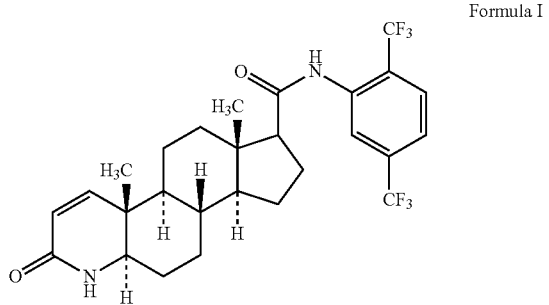

Formula I

BACKGROUND OF THE INVENTION (5α,17β)-N-[2,5-Bis(trifluoromethyl)phenyl]-3-oxo-4-azaandrost-1-ene-17-carboxamide is generically known as Dutasteride.

Dutasteride is a synthetic 4-azasteroid compound, which is a selective inhibitor of the type 1 and type 2 isoforms of steroid 5α-reductase (5AR), with which it forms a stable enzyme complex, which inhibits the conversion of testosterone to 5α-dihydrotestosterone (DHT).

Dutasteride is marketed under the name Avodart® in the US. It has been approved for the treatment of symptomatic benign prostatic hyperplasia (BPH) in men.

U.S. Pat. No. 5,565,467 disclosed Dutasteride and process for preparation. According to U.S. Pat. No. '467, Dutasteride may be prepared by reacting 3-oxo-4-androstene-17β-carboxylic acid (II) with thionyl chloride in presence of pyridine to produce 3-oxo-4-androstene-17β-carboxylic acid chloride (IIa), which is further reacted with 2,5-bis(trifluoromethyl) aniline (III) to produce 17β-N-[2,5-bis(trifluoromethyl)-phenyl]carbomoyl-1-androst-4-en-3-one (IV). Oxidation of 17β-N-[2,5-bis(trifluoromethyl)phenyl]carbomoyl-1-androst-4-en-3-one (IV) by treating with aqueous sodium permanganate and sodium periodate under basic conditions produce 17β-N-[2,5-bis(trifluoromethyl)phenyl]carbamoyl-5-oxo-A-nor-3,5-secoandrostan-3-oic acid (V), which is further treated with ammonia in ethylene glycol, followed by hydrogenation to produce 17β-N-[2,5-bis(trifluoromethyl)phenyl]carbamoyl-4-aza-5α-androstan-3-one (VI). Dehydrogenating a compound (VI) using 2,3-dichloro-5,6-dicyano-1,4-benzoquinone (DDQ) and bis(trimethylsilyl)trifluoroacetamide in dry dioxane to produce Dutasteride (I).

The process is as shown in Scheme-I below:

Scheme-I

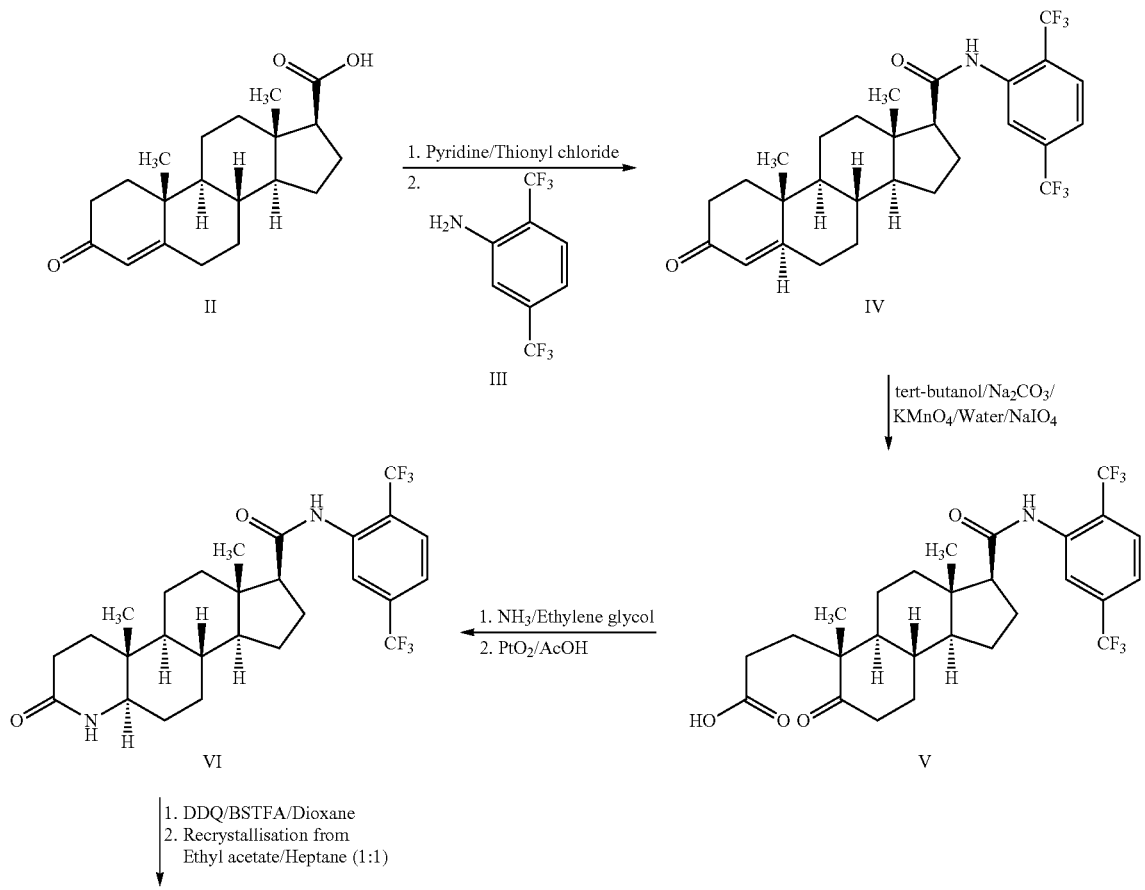

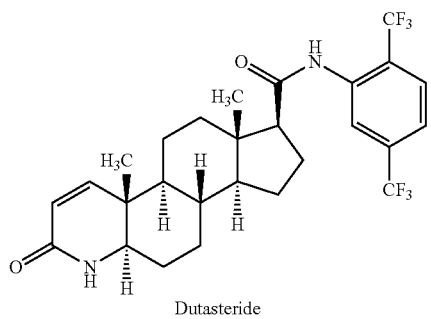

Dutasteride

U.S. Pat. No. '467 also discloses a variant process for the preparation of Dutasteride (I) by reacting 4-aza-5α-androst-1-en-3-one-17β-carboxylic acid (VII) with thionyl chloride in presence of pyridine to produce 4-aza-5α-androst-1-en-3-one-17β-carboxylic acid chloride (VIII), which is further reacted with 2,5-bis(trifluoromethyl)aniline (III) to produce Dutasteride (I).

The process is as shown in Scheme-II below:

The major disadvantage with the above process is the low yield (44%) and purity of Dutasteride (80% by HPLC) and not suitable for the preparation of Dutasteride (I) on commercial scale.

US 2005/0059692 A1 discloses a process for the preparation of Dutasteride (I), wherein 4-aza-5α-androst-1-en-3-one-17β-carboxamide (IX) is condensed with 2-iodo-1,4-bis(trifluoromethyl)benzene (X).

Scheme-II

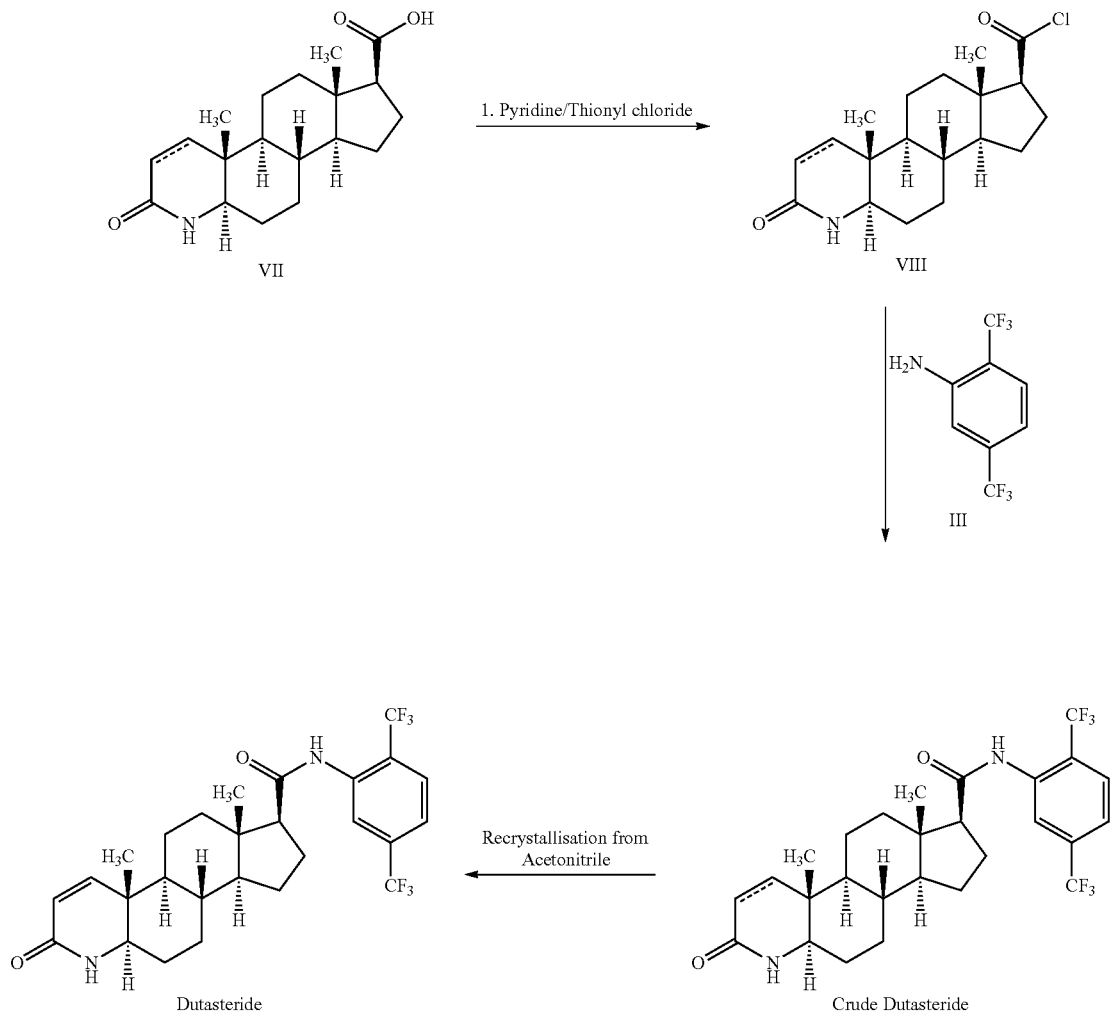

The process is as shown in Scheme-III below:

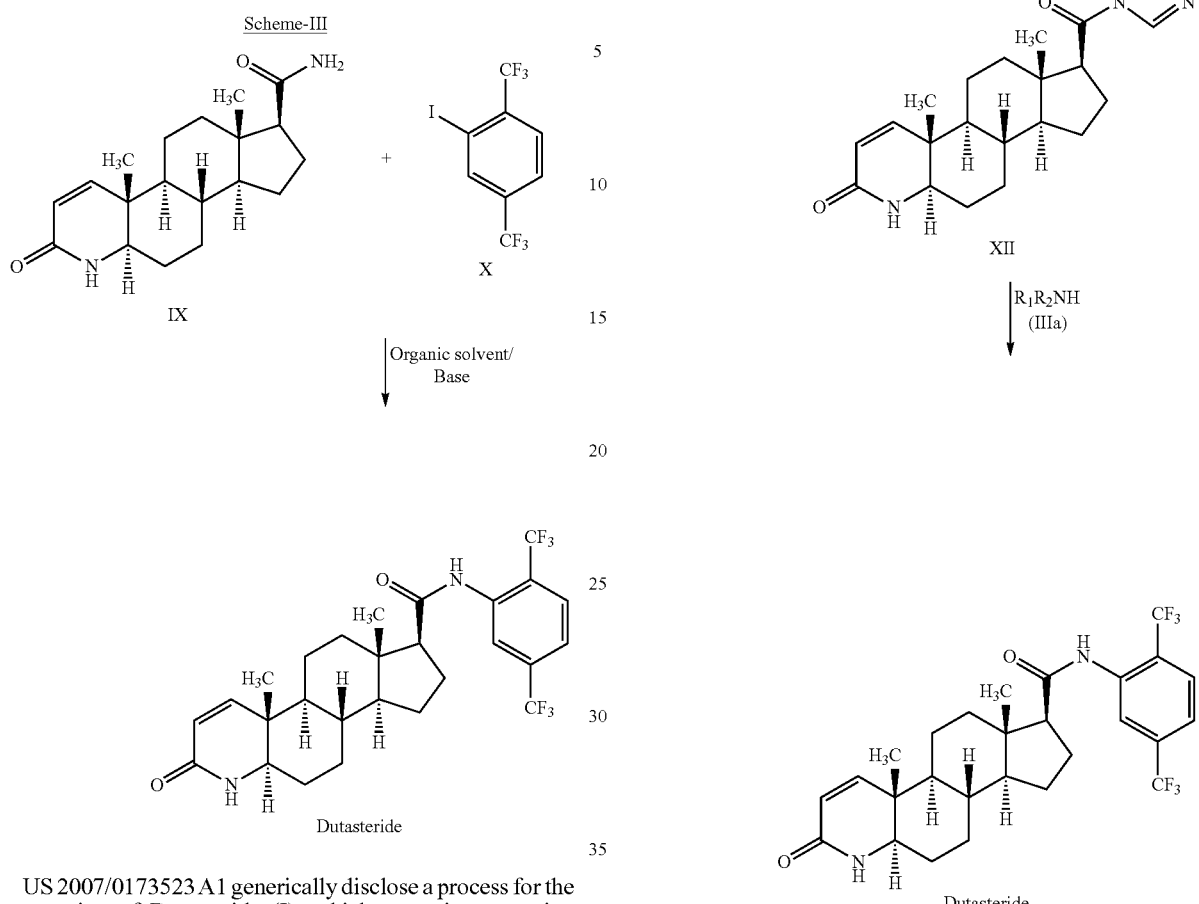

US 2007/0173523 A1 generically disclose a process for the preparation of Dutasteride (I), which comprises, reacting 4-aza-5α-androst-1-en-3-one-17β-carboxylic acid (VII) with the compound of Formula (XI) to produce an intermediate compound of Formula (XII), which is further reacted with an amine of Formula (IIIa) to produce Dutasteride (I).

The process is as shown in Scheme-IV below:

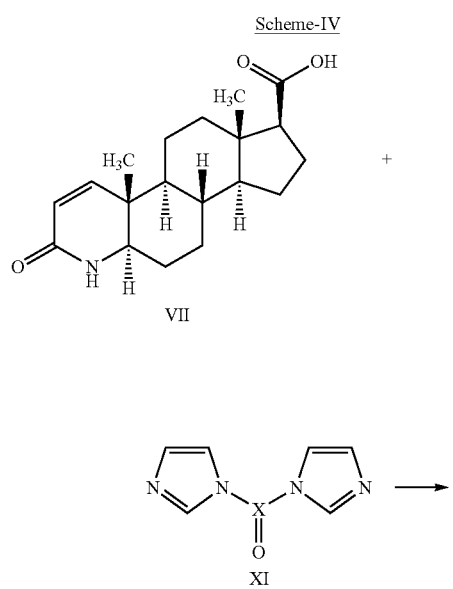

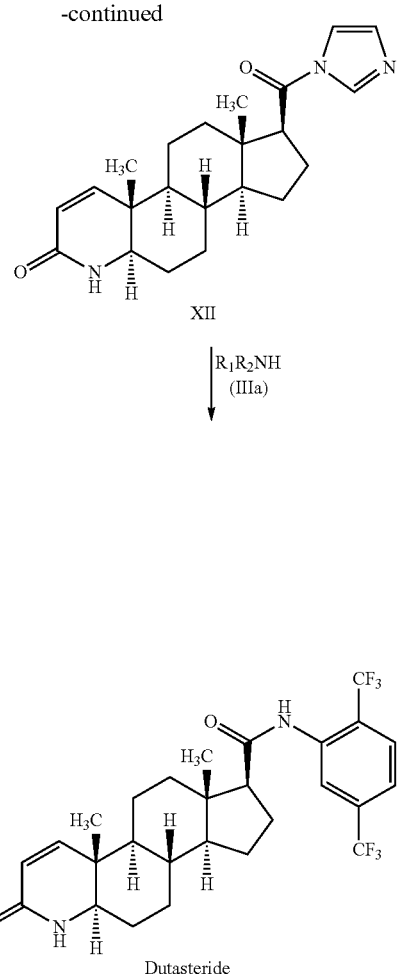

The greater stability of the intermediate XII results in slow reaction with amine IIIa, making the process difficult on commercial scale.

Hence, there is a need to develop a process, which provides Dutasteride (I) with high yields and purity on commercial scale.

The present invention is specifically directed towards a process, wherein 4-aza-5α-androst-1-en-3-one-17β-carboxylic acid (VII) is reacted with trifluoromethane sulfonic acid anhydride, before condensing with 2,5-bis(trifluoromethyl)aniline (III) to produce Dutasteride (I) of high purity and yield.

OBJECTIVE OF INVENTION

The main objective of the present invention is to provide a simple and effective process for the preparation of Dutasteride (I) with high purity and good yields on a commercial scale.

SUMMARY OF THE INVENTION

The present invention provides an improved process for the preparation of (5α,17β)-N-[2,5-bis(trifluoromethyl)phenyl]-3-oxo-4-azaandrost-1-ene-17-carboxamide of Formula (I), Formula I

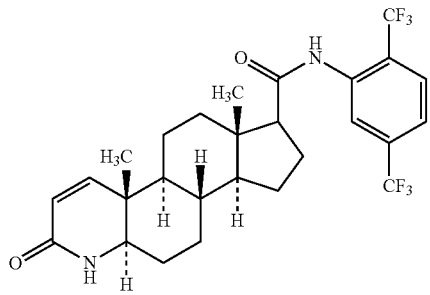

which comprises:
(i) reacting 4-aza-5α-androst-1-en-3-one-17β-carboxylic acid (VII), Formula VII

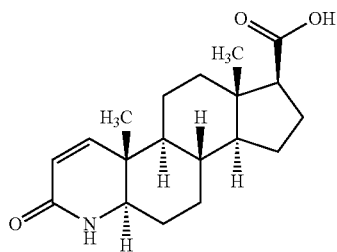

with sulfonic acid anhydride $(RSO_2)_2O$ in presence of base to produce a compound of Formula (XIII), Formula XIII

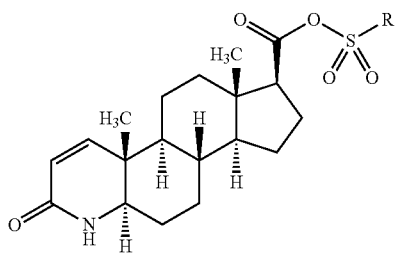

wherein R represents substituted or unsubstituted $C_{1-6}$ alkyl, $C_{1-6}$ halo alkyl, $C_{6-10}$ aryl, halo aryl;
(ii) condensing compound of Formula (XIII) with 2,5-bis (trifluoromethyl)aniline (III), Formula III

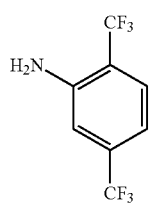

in the presence or absence of a base to produce Dutasteride (I).

DETAILED DESCRIPTION OF THE INVENTION

The present invention provides an improved process for the preparation of (5α,17β)-N-[2,5-bis(trifluoromethyl)phenyl]-3-oxo-4-azaandrost-1-ene-17-carboxamide of Formula I.

The process comprises, reacting 4-aza-5α-androst-1-en-3-one-17β-carboxylic acid (VII) with sulfonic acid anhydride in the presence of base selected from pyridine, 4-dimethylaminopyridine, triethylamine, diisopropylethylamine to produce a compound of Formula (XIII). The sulfonic acid anhydride is selected from methanesulfonic acid anhydride, ethanesulfonic acid anhydride, benzenesulfonic acid anhydride, p-toluenesulfonic acid anhydride, trifluoromethane sulphonic acid anhydride, p-nitrobenzenesulfonic acid anhydride. Preferred sulfonic acid anhydride is trifluoromethane sulphonic acid anhydride.

The reaction is carried out in a solvent selected from halogenated hydrocarbon solvents such as methylene chloride, dichloro ethane, chloroform, polar aprotic solvents such as N,N-dimethylformamide, dimethylsulfoxide, N,N'-dimethylacetamide, sulfolane or aromatic hydrocarbons such as toluene, xylene, mesitylene or mixtures thereof. Preferred solvent is the mixture of methylene chloride and N,N-dimethylformamide. The reaction may be performed at a temperature ranging from about 0° C. to about 50° C. based on the solvents used for the reaction. The reagent trifluoromethane sulfonic acid anhydride is added to the solution of 4-aza-5α-androst-1-en-3-one-17β-carboxylic acid (VII) in the organic solvent. More preferably, the reagent is added slowly in a drop-wise manner. Most preferably, the addition is carried out while maintaining the reaction mixture at a temperature of about 0° C. to about 10° C.

The sufficient period of time necessary for obtaining compound (XIII) will depend on the parameters of the reaction. Preferably, maintaining the reaction mixture for about 15 min to about 1 hour. More preferably, the reaction mixture is maintained for about 30 min to about 45 min.

The compound (XIII) is obtained by the above process can be used as such for the next step without isolating from the reaction mixture or isolated from the reaction mixture by precipitation of compound (XIII) from the reaction mixture or by removing the solvent from the reaction mixture.

The compound (XIII) is reacted with 2,5-bis(trifluoromethyl)aniline (III) in the absence or presence of suitable base to produce (5α,17β)-N-[2,5-bis(trifluoromethyl)phenyl]-3-oxo-4-azaandrost-1-ene-17-carboxamide (Dutasteride) (I). The suitable base used in the reaction is selected from an organic base such as morpholine, N-methylmorpholine, N-ethylmorpholine, 4-dimethylaminopyridine, N,N'-diisopropylethylamine, pyridine, triethylamine; inorganic base such as alkali carbonate, preferably, sodium carbonate, potassium carbonate, cesium carbonate, sodium bicarbonate or potassium carbonate, alkali metal hydroxides such as sodium hydroxide, potassium hydroxide, cesium hydroxide, magnesium hydroxide or mixtures thereof.

The reaction may be carried out in the presence of a solvent selected from an organic solvent such as halogenated hydrocarbon solvents such as methylene chloride, dichloro ethane, chloroform, polar aprotic solvents such as N,N-dimethylformamide, dimethylsulfoxide, N,N'-dimethylacetamide, sulfolane or aromatic hydrocarbons such as toluene, xylene, mesitylene or mixtures thereof. Preferred solvent is the mixture of methylene chloride and N,N-dimethylformamide. The reaction may be performed at a temperature ranging from about 0° C. to about 120° C., preferably 25° C.-50° C. The reaction time is about 5 to about 24 hours, more preferably about 15 to about 20 hours. After completion of the reaction, removing the solvent from the reaction mixture to obtain a residue. The residue containing (5α,17β)-N-[2,5-bis(trifluoromethyl)phenyl]-3-oxo-4-azaandrost-1-ene-17-carboxamide (Dutasteride) (I) in a solvent selected from toluene, ethyl acetate methyl isobutyl ketone (MIBK), which is filtered off and washed with aqueous basic solution, followed by washing with aqueous acidic solution. The resulting solution was treated with carbon and isolated crude Dutasteride (I) by removing the solvent.

The process further comprises dissolving crude Dutasteride in a solvent selected from esters such as methyl acetate, ethyl acetate, propyl acetate, butyl acetate; alcohols such as methanol, ethanol, isopropanol, n-butanol and precipitating pure Dutasteride (I) by addition of anti solvent selected from heptane, hexane, toluene, xylene, acetone, MIBK etc cooling the solution to about 0-30° C., preferably 15-20° C. and isolating pure Dutasteride (I).

It has been observed that preparation of Dutasteride (I) using above reaction conditions results in 73-75% yield and has a purity of more than 98% by HPLC analysis.

4-Aza-5α-androst-1-en-3-one-17β-carboxylic acid (VII) used in the present invention may be prepared by the process disclosed in *Drugs of the Future* (1999), 24 (3), 246-253.

The following examples are provided to illustrate the invention and are merely for illustrative purpose only and should not be construed to limit the scope of the invention.

EXAMPLES

Example 1

Preparation of (5α,17β)-N-[2,5-bis(trifluoromethyl) phenyl]-3-oxo-4-azaandrost-1-ene-17-carboxamide (Dutasteride) (I)

4-Aza-5α-androst-1-en-3-one-17β-carboxylic acid (5 gm, 0.015 mol) was suspended in methylene chloride (250 ml) at 25-30° C. under nitrogen atmosphere. N,N'-Dimethylformamide (2-3 drops) was added to the above suspension followed by pyridine (3.115 gm, 0.039 mol) at 25-30° C. The above suspension was cooled to 0-5° C. and trifluoromethane sulphonic acid anhydride (8.9 gm, 0.031 mol) dissolved in methylene chloride (10 ml) was added to the above reaction mass over a period of 15-20 min. maintaining the temperature below 10° C. It was stirred for 30 min and monitored by HPLC for the formation of mixed anhydride intermediate and thereafter N-Methylmorpholine (1.91 gm, 0.081 mol) was added to the stirred reaction mass. Subsequently, 2,5-bis(trifluoromethyl)aniline (3.61 gm, 0.015 mol) was added to the above reaction mass in one lot at 25-30° C. The reaction mass was stirred for 15-18 hours at 25-30° C. and the progress of the reaction was monitored by HPLC. After completion of reaction, solvent was distilled under reduced pressure and the obtained residue was re-dissolved in toluene (150 ml) and ethyl acetate (75 ml), filtered and washed with 10% potassium hydroxide (3×25 ml) followed by 1N aqueous hydrochloric acid (50 ml). Finally the organic layer was washed with water and de-colorized with carbon enoanticromos. The crude product obtained after distillation of the organic layer at 40-45° C. under reduced pressure was further recrystallized from ethyl acetate-heptane (60 ml, 1:1) and dried at 60-65° C. for 8 hours under vacuum.

Yield: 4.2 gm.
HPLC purity: 98.35%.

Example 2

Preparation of (5α,17β)-N-[2,5-bis(trifluoromethyl) phenyl]-3-oxo-4-azaandrost-1-ene-17-carboxamide (Dutasteride) (I)

4-Aza-5α-androst-1-en-3-one-17β-carboxylic acid (2 gm, 0.006 mol) was suspended in methylene chloride (100 ml) at 25-30° C. under nitrogen atmosphere. Pyridine (1.25 gm, 0.015 mol) was added to the above suspension in one lot at 25-30° C. It was cooled to 0-5° C. and trifluoromethane sulphonic acid anhydride (3.56 gm, 0.012 mol) dissolved in methylene chloride (10 ml) was added drop wise to the above reaction mass over a period of 15-20 min. maintaining the temperature below 10° C. It was stirred for 30 min and monitored by HPLC for the formation of mixed anhydride intermediate and thereafter N-methylmorpholine (0.765 gm, 0.0075 mol) was added to the stirred reaction mass. Subsequently, 2,5-bis(trifluoromethyl)aniline (1.44 gm, 0.006 mol) was added to the above reaction mass in one lot at 25-30° C. The reaction mass was stirred for 15-18 hours at 25-30° C. and the progress of the reaction was monitored by HPLC. After completion of reaction, solvent was distilled at 30-40° C. under reduced pressure (20-50 mm Hg) to obtain an oily residue. The obtained residue was re-dissolved in toluene (60 ml) and ethyl acetate (30 ml) and washed with 10% potassium hydroxide (3×6 ml) followed by water (2×25 ml). The crude product obtained by distillation of the organic layer at 40-45° C. under reduced pressure was further recrystallized from a mixture of ethyl acetate (12 ml) and heptane (12 ml). The product obtained was dried at 60-65° C. for 8 hours under vacuum.

Yield: 2.3 gm.
HPLC purity: 98.7%

Example 3

Preparation of (5α,17β)-N-[2,5-bis(trifluoromethyl) phenyl]-3-oxo-4-azaandrost-1-ene-17carboxamide (Dutasteride) (I)

4-Aza-5α-androst-1-en-3-one-17β-carboxylic acid (2 gm, 0.006 mol) was suspended in methylene chloride (100 ml) at 25-30° C. under nitrogen atmosphere. Pyridine (1.75 gm, 0.022 mol) was added to the above suspension in one lot at 25-30° C. It was cooled to 0-5° C. and trifluoromethane sulphonic acid anhydride (3.56 gm, 0.012 mol) dissolved in methylene chloride (10 ml) was added drop wise to the above reaction mass over a period of 15-20 min. maintaining the temperature below 10° C. It was stirred for 30 min and monitored by HPLC for the formation of mixed anhydride intermediate. Subsequently, 2,5-bis(trifluoromethyl)aniline (1.44 gm, 0.006 mol) was added to the above reaction mass in one lot at 25-30° C. It was stirred for 15-18 hours at 25-30° C. and the progress of the reaction was monitored by HPLC. After completion of reaction, solvent was distilled at 30-40° C. under reduced pressure (20-50 mm Hg) to obtain an oily residue. It was re-dissolved in toluene (60 ml) and ethyl acetate (30 ml) and washed with 10% potassium hydroxide (3×6 ml) followed by water (2×25 ml). The crude product obtained by distillation of the organic layer at 40-45° C. under reduced pressure was further re-crystallized from ethyl acetate (12 ml) and heptane (12 ml). The product obtained was dried at 60-65° C. for 8 hours under vacuum.

Yield: 1.8 gm.
HPLC purity: 98.14%.

Example 4

Preparation of (5α,17β)-N-[2,5-bis(trifluoromethyl) phenyl]-3-oxo-4-azaandrost-1-ene-17-carboxamide (Dutasteride) (I)

4-Aza-5α-androst-1-en-3-one-17β-carboxylic acid (10 gm, 0.0315 mol) was suspended in methylene chloride (250 ml) at 25-30° C. under nitrogen atmosphere. Pyridine (6.23 gm, 0.078 mol) was added to the above suspension in one lot at 25-30° C. It was cooled to 0-5° C. and trifluoromethane sulphonic acid anhydride (17.8 gm, 0.063 mol) dissolved in methylene chloride (20 ml) was added drop wise to the above reaction mass over a period of 15-20 min. maintaining the temperature below 10° C. It was stirred for 30 min and monitored by HPLC for the formation of mixed anhydride intermediate and thereafter N-methylmorpholine (3.83 gm, 0.037 mol) was added at 20° C. to the stirred reaction mass. Subsequently, 2,5-bis(trifluoromethyl)aniline (1.44 gm, 0.006 mol) was added to the above reaction mass in one lot at 25-35° C. It was stirred for 5-6 hours at 25-35° C. and the progress of the reaction was monitored by HPLC. After completion of reaction, solvent was distilled at 30-40° C. under reduced pressure (20-50 mm Hg) to obtain an oily residue. It was re-dissolved in toluene (300 ml) and ethyl acetate (150 ml) and washed with 10% potassium hydroxide (3×30 ml) followed by water (2×100 ml). The crude product obtained by distillation of the organic layer at 40-45° C. under reduced pressure was further re-crystallized from ethyl acetate (12 ml) and heptane (12 ml). The product obtained was dried at 60-65° C. for 8 hours under vacuum.

Yield: 11 gm.
HPLC purity: 98.1%.

We claim:

1. A process for the preparation of (5α,17β)-N-[2,5-bis (trifluoromethyl)phenyl]-3-oxo-4-azaandrost-1-ene-17-carboxamide (Dutasteride) of Formula (I),

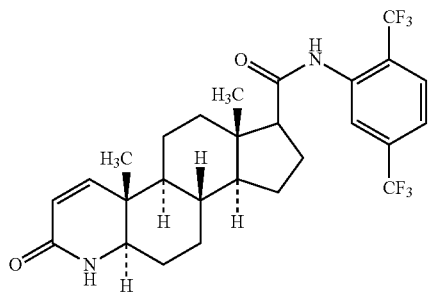

Formula I which comprises:
(i) reacting 4-aza-5α-androst-1-en-3-one-17β-carboxylic acid (VII),

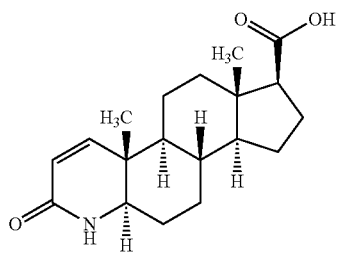

Formula VII with sulfonic acid anhydride $(RSO_2)_2O$ in presence of base in a solvent to produce a compound of Formula (XIII),

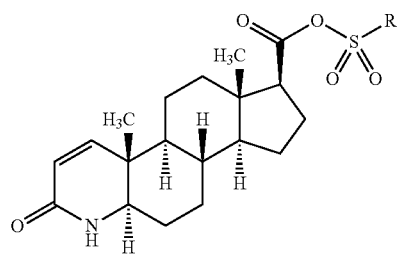

Formula XIII wherein R represents $C_{1-6}$ halo alkyl, $C_{6-10}$ halo aryl;
(ii) condensing compound of Formula (XIII) with 2,5-bis (trifluoromethyl)aniline (III),

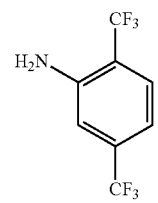

Formula III to produce Dutasteride (I).

2. The process according to claim 1, wherein the sulfonic acid anhydride is, trifluoromethane sulphonic acid anhydride.

3. The process according to claim 1, wherein the base used in step (i) is selected from the group comprising pyridine, 4-dimethylaminopyridine and triethylamine.

4. The process according to claim 1, wherein the solvent used in step (i) is an organic solvent.

5. The process according to claim 4, wherein the organic solvent is a halogenated hydrocarbon solvent selected from the group comprising methylene chloride, dichloro ethane and chloroform.

6. The process according to claim 4, wherein the organic solvent is a polar aprotic solvents selected from the group comprising N,N-dimethylformamide, dimethylsulfoxide, N,N'-dimethylacetamide, and sulfolane.

7. The process according to claim 4, wherein the organic solvent is an aromatic hydrocarbon selected from the group comprising toluene, xylene and mixtures thereof.

8. The process according to claim 1, wherein the reaction in step (ii) is carried out in the presence of a base.

9. The process according to claim 8, wherein the base used in step (ii) is an organic base selected from the group comprising morpholine, N-methylmorpholine, N-ethylmorpholine, 4-dimethylamino pyridine, N,N'-diisopropylethylamine, pyridine and triethylamine.

10. The process according to claim 8, wherein the base used in step (ii) is an inorganic base selected from an alkali carbonate or an alkali metal hydroxide.

11. The process according to claim 1, wherein the reaction in step (ii) is carried out in the presence of a solvent.

12. The process according to claim 11, wherein the solvent is selected from a halogenated hydrocarbon solvent; a polar aprotic solvent; or an aromatic hydrocarbon or mixtures thereof.

13. Compound of Formula (XIII);

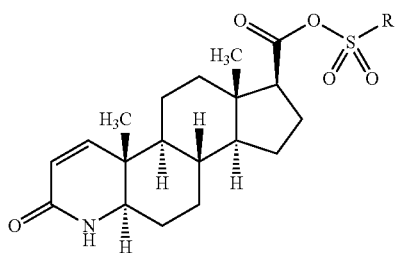

Formula XIII wherein R represents, $C_{6-10}$ halo aryl.

14. The process for the preparation of (5α,17β)-N-[2,5-bis(trifluoromethyl)phenyl]-3-oxo-4-azaandrost-1-ene-17-carboxamide (Dutasteride) of Formula (I)

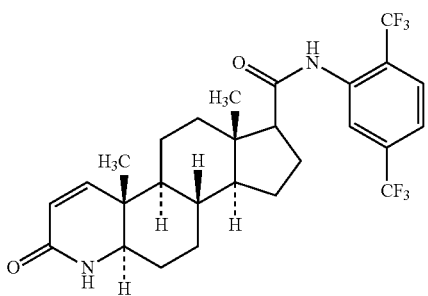

by using the compound of formula XIII

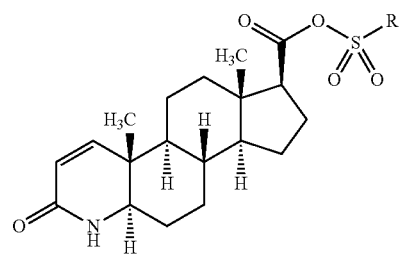

wherein R represents $C_{1-6}$ halo alkyl, $C_{6-10}$ halo aryl.

15. The process according to claim 12, wherein the halogenated hydrocarbon solvent is selected from the group comprising methylene chloride, dichloro ethane, chloroform and mixtures thereof.

16. The process according to claim 12, wherein the polar aprotic solvent is selected from the group comprising N,N-dimethylformamide, dimethylsulfoxide, N,N'-dimethylacetamide or sulfolane, or a mixture thereof.

17. The process according to claim 12, wherein the aromatic hydrocarbon is toluene or xylene, or a mixture thereof.

18. The process according to claim 10, wherein the alkali carbonate is selected from the group comprising sodium carbonate, potassium carbonate, cesium carbonate, sodium bicarbonate and potassium carbonate.

19. The process according to claim 10, wherein the alkali metal hydroxide is selected from the group comprising sodium hydroxide, potassium hydroxide, cesium hydroxide and magnesium hydroxide.

* * * * *